(12) United States Patent
Williams

(10) Patent No.: US 7,202,201 B1
(45) Date of Patent: Apr. 10, 2007

(54) FRAGRANCE EMITTING COMPOSITIONS AND PRODUCTS

(75) Inventor: Thomas L. Williams, Kingsville, MO (US)

(73) Assignee: H. E. Dan Bunch, Kansas City, MO (US)

( * ) Notice: Subject to any disclaimer, the term of this patent is extended or adjusted under 35 U.S.C. 154(b) by 0 days.

(21) Appl. No.: 11/327,892

(22) Filed: Jan. 9, 2006

(51) Int. Cl.
A61K 7/46 (2006.01)

(52) U.S. Cl. ............... 510/191; 512/1; 512/3

(58) Field of Classification Search ............ None
See application file for complete search history.

(56) References Cited

U.S. PATENT DOCUMENTS

| | | | |
|---|---|---|---|
| 4,146,402 A | 3/1979 | Kira et al. | |
| 4,146,566 A * | 3/1979 | Gaiser | 422/122 |
| 4,346,840 A * | 8/1982 | Gaiser et al. | 239/6 |
| 4,396,522 A | 8/1983 | Callicott et al. | |
| 4,629,508 A | 12/1986 | Cain, Jr. et al. | |
| 4,911,858 A | 3/1990 | Bunczk et al. | |
| 5,043,090 A | 8/1991 | Camp et al. | |
| 5,336,424 A | 8/1994 | Van Vlahakis et al. | |
| 5,415,131 A * | 5/1995 | Dodman | 119/171 |
| 5,427,711 A * | 6/1995 | Sakaguchi et al. | 510/376 |
| 5,489,415 A | 2/1996 | Van Vlahakis et al. | |
| 5,817,611 A | 10/1998 | Cooper | |
| 6,037,318 A * | 3/2000 | Na et al. | 510/379 |
| 6,268,325 B1 | 7/2001 | Luciani et al. | |
| 6,528,047 B2 | 3/2003 | Arif et al. | |
| 6,698,035 B1 | 3/2004 | Grueser | |
| 2004/0025798 A1 | 2/2004 | Lee et al. | |

* cited by examiner

*Primary Examiner*—John R. Hardee
(74) *Attorney, Agent, or Firm*—John C. McMahon

(57) ABSTRACT

Compositions and products for emitting fragrance include at least one fragrance, perlite, and sodium silicate or water glass. Compositions used to make urinal blocks and other products may further include at least one of: lime (calcium oxide), gypsum, enzymes and colorant agents. Chlorophyl and alfalfa may also be included, as well as calcium chloride, sodium chloride, potassium chloride, bicarbonate of soda, sodium sulfate, sodium talloate, nonionic surfactants, ethyl alcohol, hexylene glycol (1-hexene) ethylene glycol, propylene glycol and isopropyl alcohol.

14 Claims, 1 Drawing Sheet

FRAGRANCE EMITTING COMPOSITIONS AND PRODUCTS

BACKGROUND OF THE INVENTION

The present application relates to fragrance emitting compositions and materials made therefrom, and in particular to fragrance emitting urinal blocks and air fresheners.

Fragrance emitting products in the form of solid or semi-solid blocks, that include one or more fragrances for providing a fresh or deodorizing impression, have long been available for a variety of commercial and home applications. These applications include, for example, blocks or cakes for use in urinals, lavatories, basements closets, pet areas, lockers, storage areas and garbage cans; air freshener units equipped with small fans and refillable scented blocks; and scented urinal screen and block combinations.

For the last several decades, such fragrance emitting products have often included 1,4-dichlorobenzene (para-dichlorobenzene), also known as p-DCB, paramoth, para crystals and paracide, reflecting the use of this chemical to control moths, molds and mildew. Para-dichlorobenzene is a colorless or white crystalline solid at ambient temperature and pressure and emits an aromatic, camphor-like odor. When exposed to air, para-dichlorobenzene slowly sublimates from a solid to vapor and does not dissolve easily in water, making this chemical an efficient air deodorizer and thus a highly desirable component in air fresheners, toilet and urinal blocks. However, although there is no current evidence that moderate use of para-dichlorobenzene is harmful to human health, harmful effects have occurred from high exposures. Furthermore, the U.S. Department of Health and Human Services has determined that para-dichlorobenzene may reasonably be anticipated to be a carcinogen as animals who have been given very high levels of this chemical in water have developed liver and kidney tumors.

Thus, it is desirable to produce fragrance emitting compositions and products that do not contain para-dichlorobenzene, but that exhibit desirable qualities, such as a pleasant scent and, depending upon the product, color, cleaning and disinfecting characteristics, while dissolving or disintegrating at a rate approximately equal to the life span of such desirable characteristics, such degradation providing an indication to the user or maintenance person when the product needs to be replaced. Specifically, with respect to urinal blocks, principal requirements include that the blocks emit a fragrance and not become mushy or dissolve too quickly in water. However, it is desirable for the blocks to slowly disintegrate over time (one to two months) in a time frame that corresponds to the use of all the fragrance, so that a maintenance person will have a visual clue to replace the block. Urinal blocks may also desirably include enzymes that reduce protein and fat buildup of the urinal and plumbing connected thereto.

SUMMARY OF THE INVENTION

A composition according to the invention includes at least one fragrance, perlite, and water glass (sodium silicate). Furthermore, urinal blocks, room deodorizers and other products according to the invention may further include gypsum or lime (calcium oxide) or mixtures thereof. Additionally according to the invention, the composition may include chlorophyl or alfalfa or mixtures thereof. Dyes and enzymes may also be included in a composition according to the invention. Products made with compositions according to the invention include solid and semi-solid blocks that advantageously emit fragrance for up to about sixty days and also deteriorate near an end of the same time frame, providing a visual indicator that the product should be replaced.

OBJECTS OF THE INVENTION

Therefore, objects of the present invention include: providing fragrance emitting compositions; providing such compositions that are free of the chemical para-dichlorobenzene; providing such compositions that easily and readily compress into block (solid) or gel-like (semi-solid) form; providing a product of such compositions that dissolves or disintegrates slowly in water; providing a product of such compositions that disintegrates or deteriorates over a time span substantially equal to the life span of the desirable fragrance emitting and possibly cleaning and disinfecting characteristics thereof, to provide adequate indication of the need to replace the product; and providing such compositions and products made therefrom that are inexpensive to produce and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
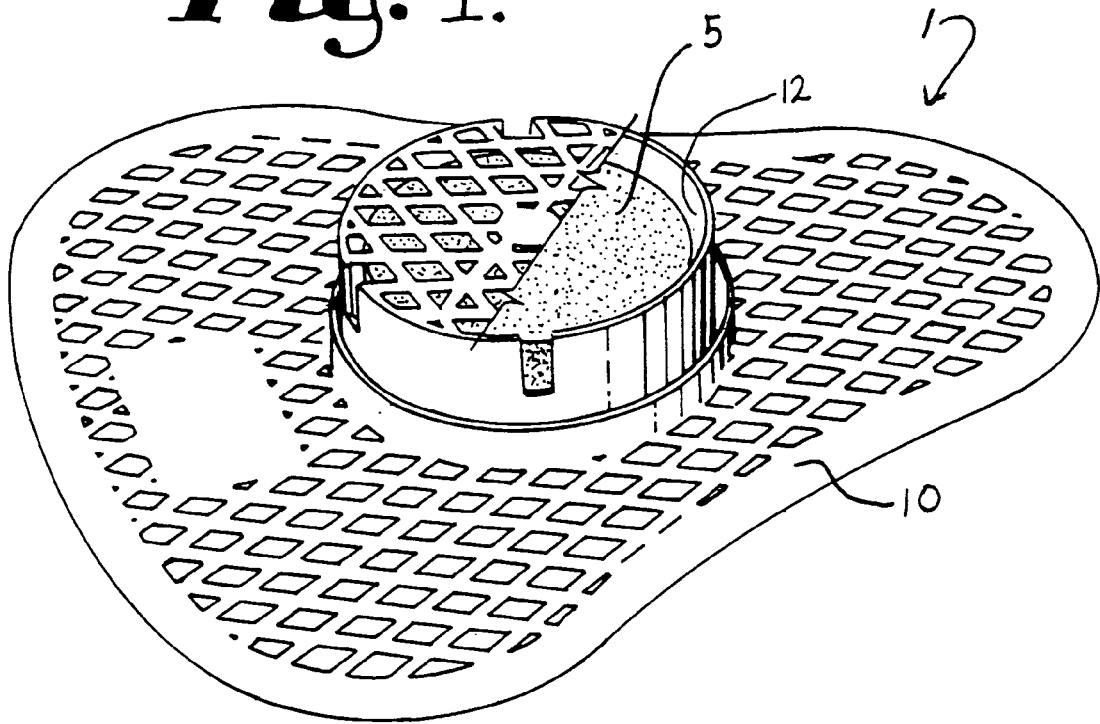
FIG. 1 is a perspective view of a solid urinal block according to the invention made by compressing a composition according to the invention and shown with a cooperating screen.
Figure 2:
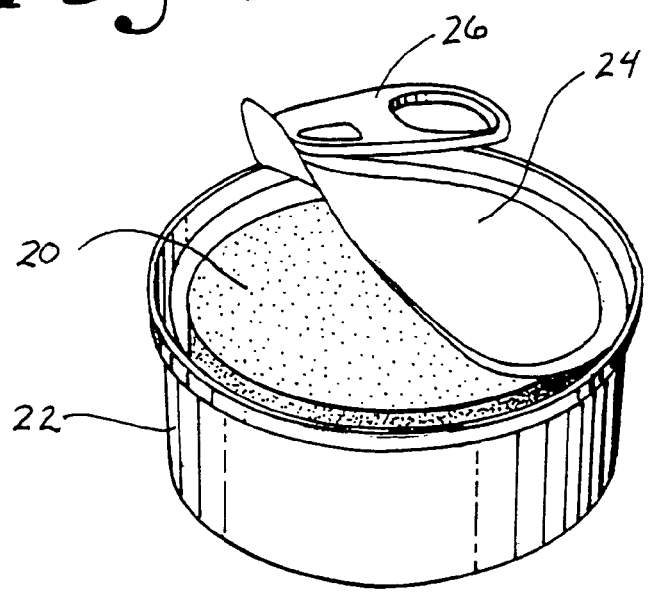
FIG. 2 is a perspective view of a semi-solid room deodorizer/air freshener according to the invention made with a composition according to the invention and shown in an opened vacuum sealed container.

With reference to FIGS. 1 and 2, the reference numeral 1 generally designates a urinal block and anti-splashback screen combination according to the invention. A urinal block or cake 5 of the invention is shown attached to a urinal anti-splashback screen 10, preferably a scented screen 10. The screen 10 is of a design known in the art and includes a cylindrical centrally located pocket 12 for holding the cylindrical block 5 in place. FIG. 2 illustrates a semi-solid or gel-like room freshener block or cake 20 according to the invention disposed in a container 22 having a vacuum lid 24 with a pull-tab 26. It is noted that solid and semi-solid blocks according to the invention may be used in a variety of applications, including, but not limited to blocks or cakes for placement in urinals, lavatories, basements, closets, pet areas, lockers, storage areas and garbage cans. Stand alone blocks according to the invention may be simply placed in a urinal (with or without a screen), on a shelf or floor, or placed in air freshener units equipped with small fans.

Compositions according to the invention used to make the scented blocks 5 and 20 and other products according to the invention, include a fragrance, perlite, and sodium silicate (water glass). Preferably, compositions according to the invention include the following: between about 3 wt. % and about 11 wt. % perlite; between about 9 wt. % and about 21 wt. % of a fragrance; and between about 60 wt. % and about 80 wt. % sodium silicate.

The fragrance component of the inventive composition may be any material, preferably in liquid or powder form, that emits an acceptable odor. Such fragrances may include, but are not limited to of a variety of well known fragrances or perfumes, including cherry, lemon, pine, orange, strawberry, lilac, cinnamon, lavender, honeysuckle, and vanilla. The fragrance component may also be an essential oil or pine extract.

Furthermore, the fragrance component may include alfalfa, a perennial plant, having a clover-like scent, added to the composition in powdered form in amounts between about 1 wt. % and about 5 wt. %. A preferred perfume/deodorizing block according to the invention is made from a composition that includes about 1 wt. % powdered alfalfa and chlorophyl. It is believed that in addition to providing fragrance, alfalfa may provide binding and enzymatic cleaning characteristics to the composition.

When compositions of the invention are formed into urinal blocks, typically the fragrance component ranges between about 7 wt. % and about 30 wt. % of the composition. When compositions of the invention are formed into room deodorizer or air freshener blocks, the fragrance component is increased, typically from about 14 wt. % up to about 30 wt. % of the entire composition.

The perlite component of the inventive composition is expanded perlite having a bulk density (loose weight) of about 2–25 lb/ft$^3$ (32–400 kg/m$^3$), preferably about 16 to about 28 lb/ft$^3$. A fine grade or mesh is preferred. Perlite is a naturally occurring siliceous rock or volcanic glass, classified as chemically inert and having a pH of about 7. Perlite is different from other volcanic glasses in that when heated to a softening range point, the crude perlite rock expands from four to twenty times an original volume thereof. The expansion process is due to the presence of water in the crude perlite rock, with the water vaporizing to create a plethora of tiny bubbles, resulting in expanded perlite weighing as little as 2 lb/ft$^3$. Expanded perlite is extremely porous and thus well suited for absorbing fragrance. In particular, the pervious nature of the expanded perlite provides open passageways in the fragrance emitting blocks 5 and 20, allowing fragrance to be given off gradually over time. Furthermore, the expanded perlite gives the blocks 5 and 20 an appearance and feel of prior art blocks made with para-dichlorobenzene with the blocks emitting a desired amount of fragrance, and/or cleaning and disinfecting properties, during the life of the block.

The sodium silicate or water glass component, is a colorless, transparent, glasslike substance commercially available in powder form or as a viscous solution in water. Chemically, the water glass component may be substantially sodium silicate or may be a mixture of sodium silicate and potassium silicate. Water glass is made by fusing sodium or potassium carbonate with sand or by heating sodium or potassium hydroxide with sand under pressure. Water glass has a high melting point (above 800° C.) and is water soluble. A preferred sodium silicate water glass component for use in the present invention has a weight ratio of $Na_2O$ to $SiO_2$ of 1:3.25. The adhesive and or binding characteristics of sodium silicate or water glass provide advantageous binding and fixing of the components of the blocks 5 and 20 and other products made with compositions of the invention.

Compositions and products according to the invention may further include one or more of the following: lime, gypsum, one or more colorant agents and one or more enzymes. A further composition according to the invention includes at least one of chlorophyl and alfalfa.

The lime component (calcium oxide) of certain compositions and products of the invention preferably ranges between about 2 wt. % and about 7 wt. % of the composition. The lime utilized in the inventive compositions and products is of commercial grade. It is believed that lime advantageously provides germicidal action, particularly desirable when the composition is formed into a urinal block 5.

The gypsum component of certain compositions and products according to the invention, chemically $CaSO_4.2H_2O$, is of commercial grade. The gypsum component preferably ranges between about 2 wt. % and about 7 wt. % of the composition. Often, the gypsum and lime components are both added to compositions of the invention, and in equal amounts. Addition of gypsum and/or lime to the composition results in products that hold a desired form upon compression, for example, such as the cylindrically shaped urinal block 5 illustrated in FIG. 1.

The colorant agent component of certain compositions and products of the invention may be of a variety of readily available dyes and pigments, sold commercially, preferably in powder or liquid form. The colorant agent is added until a desired color is obtained, typically in amounts ranging between about 0.5 wt. % and about 2.5 wt. % of the composition.

Certain preferred compositions of the invention include chlorophyl, preferably in liquid form in amounts ranging from between about 0.5 wt. % and about 5 wt. %. A particularly preferred composition includes about 0.6 wt. % chlorophyl of the total composition. The intense color of chlorophyl is useful in coloring compositions of the invention to provide a green color. Particularly when liquid chlorophyl and alfalfa are added to compositions of the invention, a pleasant green color results, and thus no other colorant agent is added. Furthermore, it is believed that chlorophyl may provide advantageous enzymatic cleaning properties.

The enzyme component of certain compositions and products according to the invention is typically a lipase or a protease and preferably a lipase and protease combination in a small amount, typically in an amount between about 0.4 wt. % and about 0.7 wt. % of the total composition. As indicated earlier, enzymes, and in particular, lipases break down fat. Furthermore, proteases break down proteins. Thus it is believed that both enzyme components work together to break down organic materials, including hair, fats, soap, waste and scum in urinals and associated plumbing. For compositions of the invention that include chlorophyl and/or alfalfa, the enzyme component may be reduced or eliminated.

In some embodiments it may be desirable to add a small amount of a hygroscopic substance to the composition, such as magnesium sulfate, calcium chloride, sodium chloride, potassium chloride, bicarbonate of soda and sodium sulfate. It is believed that the magnesium sulfate and other salts listed above bind with the sodium silicate and help the resulting product to dissipate at a desirable rate approximately equivalent to the life span of the fragrance.

When making the blocks 5 and 20 according to the invention, upon mixing, the composition is typically free flowing. The blocks then set up over time, typically up to about twenty-four hours, and may require some compression to form a solid block. If compression is required, only about 60 p.s.i. to about 100 p.s.i. (about 4 kg/cm$^2$ to about 7 kg/cm$^2$) is desired, as it is undesirable to crush or break up the perlite in the composition.

Urinal blocks according to the invention advantageously disintegrate over thirty to about sixty days of use, the deteriorated block providing a visual indication that the block should be replaced. Other agents that may be added to mixtures according to the invention to aid urinal and other fragrance emitting blocks according to the invention in releasing fragrance include, but are not limited to: sodium talloate, nonionic surfactants, ethyl alcohol, hexylene glycol (1-hexene), ethylene glycol, propylene glycol and isopropyl alcohol The following examples of compositions according to the invention are provided for illustration. All parts and percentages are by weight of the composition unless otherwise indicated.

EXAMPLE 1

| Component | Approximate Amounts wt % |
|---|---|
| Enzyme[1] | 0.4 |
| Perlite | 5.6 |
| Lime | 3.7 |
| Gypsum | 3.7 |

[1]Enzyme was a mixture of lipase and protease available from Biologix Products Group.

The above ingredients were mixed and the following ingredients were added:

| Component | Approximate Amounts wt % |
|---|---|
| Pine Forest fragrance | 9.7 |
| Green Solvisol No. 206-036-51 from Keystone Aniline Corp. | 1.9 |

The above ingredients were mixed and the following ingredient was then mixed in:

| Component | Approximate Amount wt % |
|---|---|
| Sodium Silicate | 75 |

The resulting composition was metered into a die cavity and lightly compressed with a fitting plunger die (about 60 p.s.i. to about 100 p.s.i. (about 4 kg/cm$^2$ to about 7 kg/cm$^2$), yielding urinal blocks.

| Component | Approximate Amounts wt % |
|---|---|
| Perlite | 6.2 |
| Gypsum | 6.2 |
| Lime | 6.2 |

The above ingredients were mixed and the following ingredients were added:

EXAMPLE 2

| Component | Approximate Amounts wt % |
|---|---|
| Perfume | 14.6 |
| Liquid Chlorophyl | 0.6 |
| Powder Alfalfa | 1.0 |

The above ingredients were mixed and the following ingredient was then mixed in:

| Component | Approximate Amount wt % |
|---|---|
| Sodium Silicate[1] | 65.2 |

[1]Weight ratio of Na$_2$O to SiO$_2$ of 1:3.25 and density of 41° Be' (degrees Baume') (equivalent specific gravity of 1.3942).

The resulting composition was metered into a die cavity and lightly compressed with a fitting plunger die (about 60 p.s.i. to about 100 p.s.i. (about 4 kg/cm$^2$ to about 7 kg/cm$^2$), yielding urinal blocks.

EXAMPLE 3

| Component | Approximate Amounts wt % |
|---|---|
| Perlite | 6.9 |
| Red Dye Keystone No. 606-26-50 Keystone Aniline Corp. | 1.4 |
| Cherry Fragrance | 19.0 |
| Gypsum | 3.5 |

The above ingredients were mixed and the following ingredient was mixed in:

| Component | Approximate Amount wt % |
|---|---|
| Sodium Silicate | 69.2 |

The resulting composition was metered into a die cavity and lightly compressed with a fitting plunger die (about 60 p.s.i. to about 100 p.s.i. (about 4 kg/cm$^2$ to about 7 kg/cm$^2$), yielding perfume/air freshening blocks.

EXAMPLE 4

| Component | Approximate Amounts wt % |
|---|---|
| Perlite | 6.0 |
| Yellow Dye Solvisol No. 806-056-50 from Keystone Aniline Corp. | 1.8 |
| Lemon Fragrance | 19.9 |
| Gypsum | 6.0 |

The above ingredients were mixed and the following ingredients were mixed in:

| Component | Approximate Amount wt % |
|---|---|
| Water | 6.8 |
| Sodium Silicate | 59.5 |

The resulting composition was metered into a die cavity and lightly compressed with a fitting plunger die (about 60 p.s.i. to about 100 p.s.i. (about 4 kg/cm$^2$ to about 7 kg/cm$^2$), yielding perfume/air freshening blocks.

EXAMPLE 5

| Component | Approximate Amounts wt % |
|---|---|
| Sodium Talloate | 9.8 |
| H$_2$O | 19.6 |

The above ingredients were heated and mixed and the following was mixed in and heated:

| Component | Approximate Amounts wt % |
|---|---|
| Sodium Silicate | 23.5 |

The following ingredients were then mixed in:

| Component | Approximate Amount wt % |
|---|---|
| Ethyl Alcohol | 2.9 |
| Propylene Glycol | 8.8 |
| Red Cherry Fragrance | 31.1 |

The following was then mixed in:

| Component | Approximate Amounts wt % |
|---|---|
| Perlite | 4.3 |

The resulting composition was metered into a die cavity and lightly compressed with a fitting plunger die (about 60 p.s.i. to about 100 p.s.i. (about 4 kg/cm$^2$ to about 7 kg/cm$^2$), yielding urinal blocks.

EXAMPLE 6

| Component | Approximate Amounts wt % |
|---|---|
| Perlite | 9.9 |
| Lime | 4.0 |
| Magnesium Sulfate | 0.7 |
| Sodium Sulfate | 0.7 |
| Hexylene Glycol | 3.3 |
| Yellow Dye Solvisol No. 806-056-50 of Keystone Aniline Corp. | 1.0 |
| Perfume | 10.0 |

The above ingredients were mixed and the following ingredient was mixed in:

| Component | Approximate Amount wt % |
|---|---|
| Sodium Silicate | 70.4 |

The resulting composition was metered into a die cavity and lightly compressed with a fitting plunger die (about 60 p.s.i. to about 100 p.s.i. (about 4 kg/cm$^2$ to about 7 kg/cm$^2$), yielding urinal blocks.

EXAMPLE 7

| Component | Approximate Amounts wt % |
|---|---|
| Perlite | 10.3 |
| Lime | 4.3 |
| Gypsum | 4.3 |

The above ingredients were mixed and the following ingredients were mixed in:

| Component | Approximate Amount wt % |
|---|---|
| Green Dye Solvisol blue No. 206-036-51 and Solvisol Yellow No. 806-056-50 - 50% each by weight of Keystone Aniline Corp. | 0.8 |
| Propylene Glycol | 0.4 |
| Nonionic Surfactant[1] | 0.8 |

[1]T-Det-9.5 manufactured by Huntsman Chemical.

The above ingredients were mixed and the following ingredient was mixed in:

| Component | Approximate Amount wt % |
|---|---|
| Sodium Silicate | 79.1 |

The resulting composition was metered into a die cavity and lightly compressed with a fitting plunger die (about 60 p.s.i. to about 100 p.s.i. (about 4 kg/cm$^2$ to about 7 kg/cm$^2$), yielding urinal blocks.

It is to be understood that while certain forms of the present invention have been illustrated and described herein, it is not to be limited to the specific forms or arrangement of parts described and shown.

What is claimed and desired to be secured by Letters Patent is as follows:

1. A fragrance emitting composition comprising:
    a) between about 3 wt. % and about 11 wt. % perlite;
    b) between about 60 wt. % and about 80 wt. % water glass; and
    c) between about 9 wt. % and about 30 wt. % of a fragrance.

2. The composition of claim 1 further comprising at least one of lime and gypsum and mixtures thereof.

3. The composition of claim 1 further comprising at least one of chlorophyl and alfalfa and mixtures thereof.

4. The composition of claim 1 further comprising an enzyme.

5. A fragrance emitting composition comprising:
    a) between about 3 wt. % and about 11 wt. % perlite;
    b) between about 9 wt. % and about 30 wt. % of a fragrance;
    c) between about 60 wt. % and about 80 wt. % water glass; and
    d) between about 2 wt. % and about 7 wt. % gypsum.

6. The composition of claim 5 further comprising between about 2 wt. % and about 7 wt. % lime.

7. The composition of claim 5 further comprising between about 0.5 wt. % and about 2.5 wt. % of a colorant agent.

8. The composition of claim 5 further comprising between about 0.4 wt. % and about 0.7 wt. % of an enzyme.

9. The composition of claim 8 wherein the enzyme is selected from the group consisting of lipase and protease and mixtures thereof.

10. A fragrance emitting composition comprising:
    a) between about 3 wt. % and about 11 wt. % perlite;
    b) between about 9 wt. % and about 30 wt. % of a fragrance;
    c) between about 60 wt. % and about 80 wt. % sodium silicate;
    d) between about 2 wt. % and about 7 wt. % gypsum; and
    e) between about 2 wt. % and about 7 wt. % lime.

11. The composition of claim 10 further comprising chlorophyl.

12. The composition of claim 10 further comprising alfalfa.

13. A kit comprising:
    a) a urinal screen; and
    b) a urinal block formed from a composition comprising:
        i) between about 3 wt. % and about 11 wt. % perlite;
        ii) between about 9 wt. % and about 30 wt. % of a fragrance;
        iii) between about 60 wt. % and about 80 wt. % sodium silicate; and
        iv) between about 2 wt. % and about 14 wt. % gypsum.

14. The kit of claim 13 wherein the composition further comprises between about 2 wt. % and about 14 wt. % lime.

* * * * *